(12) United States Patent
Suzuki (10) Patent No.: US 8,870,378 B2
(45) Date of Patent: Oct. 28, 2014

(54) OPHTHALMIC MEASUREMENT DEVICE

(75) Inventor: Takayoshi Suzuki, Hamamatsu (JP)

(73) Assignee: Kowa Company, Ltd. (JP)

( * ) Notice: Subject to any disclaimer, the term of this patent is extended or adjusted under 35 U.S.C. 154(b) by 9 days.

(21) Appl. No.: 13/395,400

(22) PCT Filed: Sep. 10, 2009

(86) PCT No.: PCT/JP2009/065842
§ 371 (c)(1),
(2), (4) Date: Mar. 23, 2012

(87) PCT Pub. No.: WO2011/030426
PCT Pub. Date: Mar. 17, 2011

(65) Prior Publication Data
US 2012/0200826 A1    Aug. 9, 2012

(51) Int. Cl.
*A61B 3/00*  (2006.01)
*A61B 3/15*  (2006.01)

(52) U.S. Cl.
CPC .............. *A61B 3/0075* (2013.01); *A61B 3/152* (2013.01)
USPC ............................................ 351/208; 396/18

(58) Field of Classification Search
CPC ........ A61B 3/145; A61B 3/152; A61B 3/165; A61B 3/102; A61B 5/0033; A61B 5/0035; A61B 5/0037; A61B 5/0073; A61B 8/13; A61B 3/0075
USPC ..................................... 351/200–246; 396/18
See application file for complete search history.

(56) References Cited

U.S. PATENT DOCUMENTS

| | | | |
|---|---|---|---|
| 5,596,377 A | 1/1997 | Yano | |
| 5,610,672 A | 3/1997 | Hirono et al. | |
| 6,053,614 A * | 4/2000 | Kawamura et al. | 351/211 |
| 7,293,874 B2 * | 11/2007 | Suzuki et al. | 351/208 |
| 2004/0183997 A1 | 9/2004 | Suzuki | |
| 2005/0179867 A1 | 8/2005 | Suzuki et al. | |

FOREIGN PATENT DOCUMENTS

| | | |
|---|---|---|
| JP | 64-017623 | 1/1989 |
| JP | 7-178052 | 7/1995 |
| JP | 8-103414 | 4/1996 |
| JP | 2004-275503 | 10/2004 |
| JP | 2004-275504 | 10/2004 |
| JP | 2005-224430 | 8/2005 |

* cited by examiner

*Primary Examiner* — Darryl J Collins
*Assistant Examiner* — Gary O'Neil
(74) *Attorney, Agent, or Firm* — Knobbe Martens Olson & Bear LLP (57) ABSTRACT

Provided is a technique that makes it possible to carry out more accurately alignment of a device optical system by a simpler method in measuring an optical characteristic at an anterior ocular segment of an eye of examinee's by an ophthalmic measurement device. In measuring an optical characteristic at an anterior ocular segment of an eye (A) of examinee's, an adjustment of positional relationship between the eye (A) of examinee's and a measurement optical system is carried out by utilizing reflection lights (B, C, D), i.e., the light (B) generated by reflection of the irradiated light from the infrared L.E.D. (11) at the cornea, the light (C) generated by reflection of the laser light (E) from a laser light source at the cornea, and the light (D) generated by reflection of the laser light (E) from the laser light source at the crystalline lens.

8 Claims, 10 Drawing Sheets

| N | BG | (%) | FLARE | WA |
|---|-----|-----|-------|----|
| 1 | 14.7 | 1 | 17.0 | |
| 2 | 14.1 | 0 | 16.9 | C |
| 3 | 26.3 | 33 | 10.0 | B |
| 4 | 14.4 | 0 | 18.0 | |
| 5 | 15.4 | 3 | 17.2 | |
| 6 | 30.8 | 0 | 17.1 | S |
| 7 | 18.7 | 1 | 19.1 | |
| 8 | 17.5 | 0 | 19.3 | |
| | AV. | | 16.8 | |
| | S.D. | | 2.9 | |

OPHTHALMIC MEASUREMENT DEVICE

CROSS-REFERENCE TO RELATED APPLICATIONS

This application is the U.S. National Phase under 35 U.S.C. §371 of International Application PCT/JP2009/065842, filed Sep. 10, 2009, which was published in a non-English language.

TECHNICAL FIELD

The present invention relates to an ophthalmic measurement device that measures optical characteristics of an anterior segment of an eye of an examinee, e.g., to enable to quantify a protein concentration or the like in aqueous humor of the examinee's eye. More specifically, the present invention relates to an ophthalmic measurement device that is improved in a positional adjustment (alignment) between the examinee's eye and the measurement device.

BACKGROUND ART

A protein concentration (flare) and a cell number density in an anterior chamber of an eye reflect conditions of various disorders including a postoperative inflammation. Quantitative measurement of these is of clinical importance. As a method for measuring them quantitatively is known a method of irradiating an anterior ocular segment of an examinee with a laser light beam from a laser light source, receiving at a light receiving unit scattered light of the laser light beam from the anterior ocular segment, converting it into an electric signal, and deriving optical characteristics of the anterior ocular segment from this electric signal.

As a measurement device for use in such a measurement method is known an ophthalmic measurement device provided with a monitor photographing unit, receiving at the monitor photographing unit a virtual image of scattered light of a laser light beam emitted to an examinee's eye by a surface of a cornea, and the scattered light of the laser light beam, and carrying out a positional adjustment (alignment) between a laser light source and the photographing unit in accordance with positions of the virtual image and the scattered light at the monitor photographing unit (for example, refer to Patent Literature 1).

Also known is an ophthalmic measurement device carrying out alignment with reference to a corneal apex which is different from optical compositions of a light projecting system and a light receiving system. In the alignment, an intersecting point of optical axes of the light projecting system and the light receiving system in an examinee's eye is set as a biologic characteristic measuring point in the examinee's eye displaced as much as a predetermined distance from the corneal apex (for example, refer to Patent Literature 2).

Further known is an ophthalmic measurement device integrally provided at a measuring unit with a semiconductor laser irradiating an anterior ocular segment of an examinee's eye with a laser light beam at an angle of 30°, a high-sensitivity light receiving device receiving scattered light of a laser light beam having an angle of 60° and converting it into an electric signal, a calculating unit calculating optical characteristics of the anterior ocular segment from the electric signal, an infrared LED irradiating the examinee's eye with light from a front, a CCD photographing the examinee's eye from the front, an infrared LED irradiating the examinee's eye with light approximately at an angle of 30°, and a CCD photographing the examinee's eye at an angle of 60°. In this device, based on first and second virtual images by the two CCDs, a base is moved to adjust positional relationship between the examinee's eye and the measuring unit (for example, refer to Patent Literature 2).

In the aforementioned measurement methods, a positional adjustment (alignment) between the laser light source and the light receiving unit and the examinee's eye is important for accurate measurement of the anterior ocular segment. However, the aforementioned respective measurement devices have problems in the aforementioned accurate alignment.

For example, some of the aforementioned ophthalmic measurement devices have difficulty in increasing the accuracy of the alignment since only the reflection light at the corneal apex is referred to, and others possibly give the examinee a sense of anxiety since a position irradiated with the laser light cannot be checked. Also, in the device in which the anterior ocular segment of the examinee's eye is observed obliquely to carry out alignment, positional relationship between an examiner and the examinee differs from how the observed examinee's eye looks, which makes it difficult to operate the alignment in some cases. Further, in the device that requires alignment in two steps, there is a case in which alignment operations are complicated, which makes it difficult to shorten alignment time.

CITATION LIST

Patent Literature

Patent Literature 1: Japanese Patent Application Laid-Open No. S64-17623
Patent Literature 2: Japanese Patent Application Laid-Open No. 2004-275503
Patent Literature 3: Japanese Patent Application Laid-Open No. 2005-224430

SUMMARY OF INVENTION

Technical Problem

The present invention is accomplished by taking such problems of the conventional techniques as mentioned above into consideration thereof, and an object thereof is to provide a technique that makes it possible to carry out a positional adjustment (alignment) between an examinee's eye and a measurement device, more accurately or more simply, in an ophthalmic measurement device measuring optical characteristics of an anterior ocular segment of an eye of an examinee.

Solution to Problem

In the present invention, in measuring optical characteristics of an anterior ocular segment of an examinee's eye, an adjustment of positional relationship between the examinee's eye and a measurement device (a measurement optical system) is carried out by utilizing reflection lights, i.e., light generated by reflection of light from a reference light source irradiating the examinee's eye with light from a front at a cornea of the examinee's eye, light generated by reflection of laser light from a laser light source irradiating the examinee's eye with light obliquely at the cornea of the examinee's eye, and light generated by reflection of the laser light at a crystalline lens of the examinee's eye.

More specifically, an ophthalmic measurement device measuring optical characteristics of an anterior ocular segment of an examinee's eye comprising a laser light source irradiating the anterior ocular segment of the examinee's eye with a laser light beam from an oblique direction to the examinee's eye, a light receiving unit receiving scattered light of the laser light beam scattered at the anterior ocular segment and converting the scattered light into an electric signal, and a calculating unit calculating the optical characteristics of the anterior ocular segment from the electric signal further comprises a reference light source irradiating the examinee's eye with light from a front of the examinee's eye, a photographing means photographing the examinee's eye, and a positional adjusting means adjusting relative positions of an optical system including the laser light source, the light receiving unit, the reference light source, and the photographing means and the examinee's eye, and in adjustment of relative positions of the examinee's eye and the optical system by the positional adjusting means, the relative positions are adjusted by utilizing first reflection light generated by reflection of light emitted from the reference light source at a cornea of the examinee's eye, second reflection light generated by reflection of laser light emitted from the laser light source at the cornea of the examinee's eye, and third reflection light generated by reflection of laser light emitted from the laser light source at a crystalline lens of the examinee's eye.

With the present invention, since a positional adjustment between the examinee's eye and the measurement device (the measurement optical system) can be carried out with reference to three kinds of reflection light, i.e., reflection light generated by reflection of irradiated light from the reference light source at the cornea of the examinee's eye, reflection light generated by reflection of irradiated light from the laser light source at the cornea of the examinee's eye, and reflection light generated by reflection of the irradiated light at the crystalline lens, alignment of the ophthalmic measurement device can be carried out more accurately without complicating operations.

Also, in the present invention, the ophthalmic measurement device further comprises a displaying unit for displaying an image photographed by the photographing means, and in adjustment of relative positions of the optical system and the examinee's eye by the positional adjusting means, the relative positions may be adjusted by approximating to respectively set target positions, on the image photographed by the photographing means and displayed on the displaying unit, a position of a first bright point corresponding to a virtual image of the reference light source based on the first reflection light generated by reflection of light emitted from the reference light source at the cornea of the examinee's eye, a position of a second bright point corresponding to the second reflection light generated by reflection of laser light emitted from the laser light source at the cornea of the examinee's eye, and a position of a third bright point corresponding to the third reflection light generated by reflection of laser light emitted from the laser light source at the crystalline lens of the examinee's eye.

By doing so, alignment of the ophthalmic measurement device can be carried out by simple operations of approximating to the target positions three bright point positions appearing on the displaying unit by the reflection light generated by reflection of irradiated light from the reference light source at the cornea of the examinee's eye and the reflection light generated by reflection of irradiated light from the laser light source at the cornea and the crystalline lens of the examinee's eye. Thus, alignment can be carried out more simply and more accurately. Also, at this time, a troublesome operation such as display switching is not needed.

Also, in the present invention, at least a target representing a target position of the first bright point may be displayed on the displaying unit. By doing so, at least the target position of the first bright point becomes clearer for an examiner, and alignment operations can be carried out more readily and more accurately.

Also, in the present invention, light emitted from the reference light source may have a wavelength in an infrared region. By doing so, inconvenience in which the examinee feels light from the reference light source too bright can be restricted, and burden on the examinee's eye can be reduced. Also, a clear virtual image can be obtained on the displaying unit as well.

Also, in the present invention, intensity of laser light emitted from the laser light source at the time of adjustment of the relative positions of the examinee's eye and the measurement device (the measurement optical system) may be lower than intensity of laser light emitted from the laser light source at the time of measurement of the optical characteristics of the examinee's eye. By doing so, intensity of light from the reference light source and intensity of light from the laser light source can be close to each other, the bright points can look alike at the time of adjusting positions of the bright points on one displaying unit, and alignment operations can be carried out more readily. At the same time, burden on the examinee's eye can be reduced.

Also, in the present invention, the photographing means may photograph the examinee's eye from a front. Since the examinee and the examiner normally face each other to perform ophthalmic measurement, a direction of positional relationship between the examinee and the examiner and a direction of display of the examinee's eye on the displaying unit can be equal, which enables the examiner to carry out the alignment operations more smoothly.

It is to be noted that the photographing means in the ophthalmic measurement device of the present invention is not particularly limited as long as it is a means that can photograph reflection light (virtual image) of the reference light source at the examinee's eye and can photograph reflection light (real image) of light from the laser light source at the examinee's eye. As the photographing means, an image sensor such as a CCD image sensor is preferable from the viewpoint of simplicity of the processing of a photographed image and the configuration.

Also, in the present invention, providing the laser light source, the light receiving unit, the reference light source, and the photographing means so that the mutual relative positions can be fixed is a prerequisite. By fixing the relative positions, positional displacement of the aforementioned first, second, and third bright points caused by displacement in positional relationship between the photographing means and each light source can be prevented, and reproducibility of alignment can be secured.

Also, the ophthalmic measurement device of the present invention includes the positional adjusting means relatively adjusting positions of the examinee's eye and the optical system including the laser light source, the light receiving unit, the reference light source, and the photographing means. This positional adjusting means may be a means for adjusting a position of the optical system with respect to the examinee's eye or a means for adjusting a position of the examinee or a face of the examinee while fixing a position of the optical system. The positional adjusting means is preferably a base that can relatively move the optical system including the laser light source, the light receiving unit, the reference light source, and the photographing means with respect to the examinee's eye from the viewpoint of carrying out accurate alignment with simple operations.

The ophthalmic measurement device of the present invention includes the displaying unit for displaying an image photographed by the photographing means. As the displaying unit, a normal displaying device for use in displaying images and information can be used. The displaying unit preferably displays optimal positions of the first, second, and third bright points as well from the viewpoint of carrying out accurate and highly reproducible alignment. The optimal positions of the first, second, and third bright points may be ones derived as theoretical values or ones obtained from an experience or an experiment although they depend on the measurement target and the measurement part. Displays of the aforementioned optimal positions may be marks put on the screen or images displayed in the screen.

The ophthalmic measurement device of the present invention may further include a recording unit in which light amounts of the reference light source and the laser light source and images of the examinee's eye by the photographing means are recorded. With such a recording unit, previous alignment information can be utilized for following alignment, which enables accurate and highly reproducible alignment. As the recording unit, a normal storage device for use in recording information can be used.

In a case where the ophthalmic measurement device of the present invention has a recording unit, the calculating unit may extract the first, second, and third bright points from an image of the examinee's eye and record information on positions of the extracted bright points on the image in the recording unit. Extraction of the respective bright points and specification of the positions on the image can be performed by known image processing techniques. Also, in this case, the ophthalmic measurement device of the present invention may have an inputting means for inputting data in the calculating unit from outside. In this case, the calculating unit can correlate the light amount of the reference light source, the image of the examinee's eye or the positional information of the first, second, and third bright points, and various data input by the inputting means with one another and can record them in the recording unit. Thus, measured data can be organized and utilized for the future easily. The various data input by the inputting means is not particularly limited as long as it identifies the examinee or the examinee's eye. Examples of such data are an identification number of the examinee and right-left display data representing whether the examinee's eye is a right eye or a left eye. As part or all of the recording unit, part or all of the calculating unit, and the inputting means, a commercially available personal computer can be used.

Also, in the ophthalmic measurement device of the present invention, in a case where the positional adjusting means is a base, information on measurement can be determined by a position of this base. Examples of the information determined by a position of the base are the right-left display data and information on whether or not the examinee has reached a position to enable alignment. Determination of such information by a position of the base can further facilitate operations of alignment and operations relating to alignment such as input of data.

Also, the ophthalmic measurement device of the present invention can be used for various kinds of measurement based on optical characteristics of the anterior ocular segment, such as a protein concentration and a cell number density in an anterior chamber of the eye, obtained from scattered light when the examinee's eye is irradiated with a laser light beam.

It is to be noted that the aforementioned solutions to the problems of the present invention can be used in combination with one another as much as possible.

Advantageous Effects of Invention

With the present invention, it is possible to carry out, more accurately or more simply, a positional adjustment (alignment) between an examinee's eye and a measurement device in an ophthalmic measurement device measuring optical characteristics of an anterior ocular segment of an eye of an examinee.

DESCRIPTION OF EMBODIMENTS

Hereinafter, embodiments of the present invention will be described with reference to the drawings.

Embodiment

Figure 1:
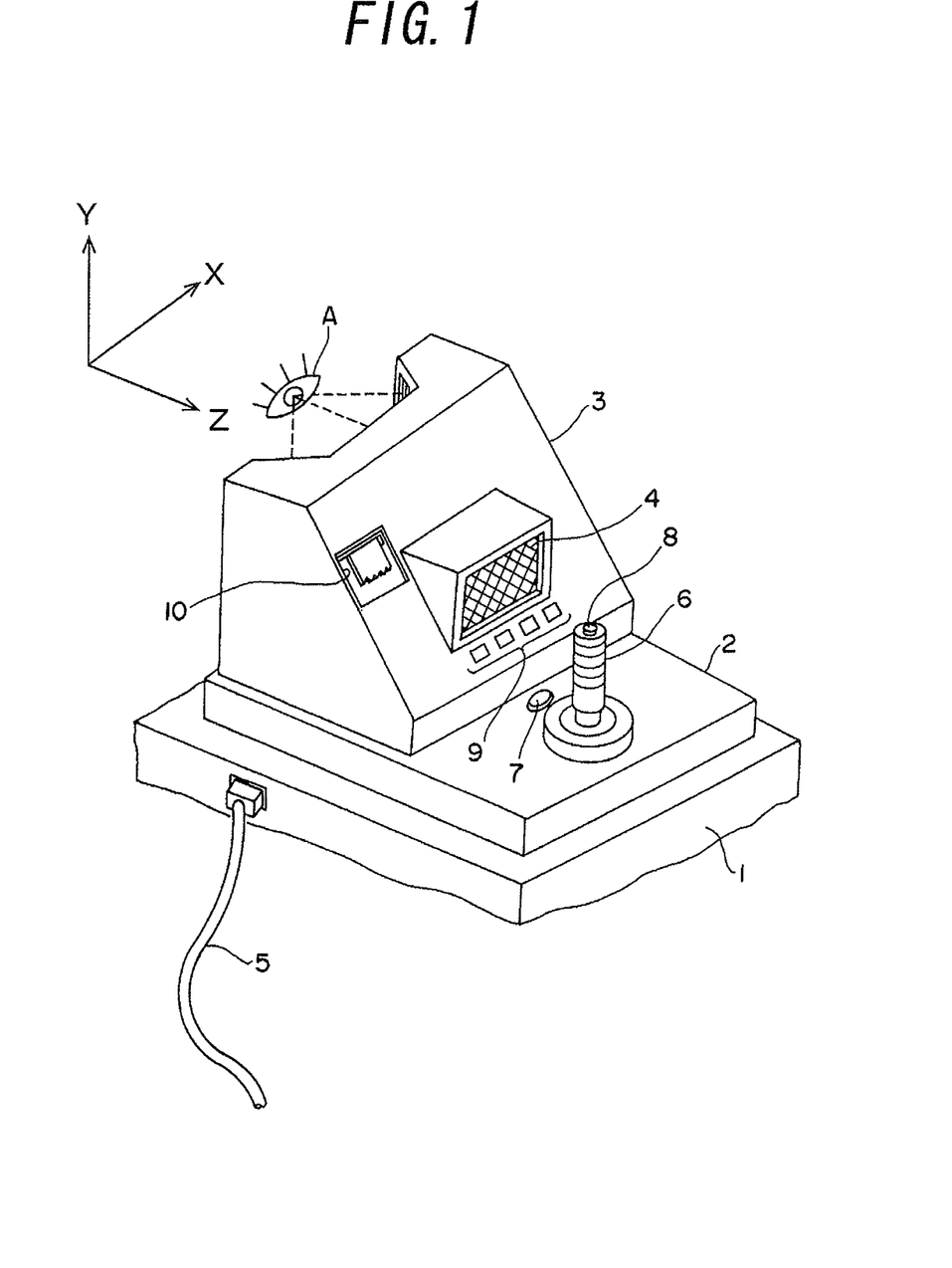
FIG. 1 illustrates an outline view of a measurement device according to an embodiment of the present invention.

An ophthalmic measurement device according to the present embodiment includes a fixed base 1, a base 2 provided to be movable on the fixed base 1, a measuring unit 3 fixed on the base 2, and a monitor 4 as a displaying unit fixed at the measuring unit 3, as illustrated in FIG. 1.

To the fixed base 1 is connected a communication cable 5 connected to a personal computer and are provided a base position detector (not illustrated in FIG. 1) detecting a position of the base 2 and a supporting base (not illustrated) supporting a face of an examinee. The base 2 is provided with a joystick 6 to move the base 2 and perform various operations at the time of alignment and a screen switching button 7 used to instruct switching of images displayed on the monitor 4. Operating this joystick 6 enables the base 2 to be moved with respect to the fixed base 1 by actuation of a motor (not illustrated). A component that moves the base 2 with respect to the fixed base 1 corresponds to a positional adjusting means in the present embodiment. At the top of the joystick 6 is provided a measuring button 8. It is to be noted that, in the following description, a horizontal direction which is a direction perpendicular to a direction of the examinee opposed to the ophthalmic measurement device is referred to as an X direction, a vertical upper direction is referred to as a Y direction, and a direction of the examinee to a side of the ophthalmic measurement device is referred to as a Z direction, as illustrated in FIG. 1.

The measuring unit 3 is provided not only with the monitor 4 but also with four function buttons 9, a not illustrated printer, a discharging port 10 to discharge a printed matter of a measurement result printed by this printer, an alignment and measurement optical system, and an alignment and measurement control system. The monitor 4 is fixed on a back surface of the measuring unit 3 facing the examinee, in a reverse direction from the examinee (to be opposed to a side of an examiner) so that the examiner can look at an image in a state of facing the examinee.

Figure 2:
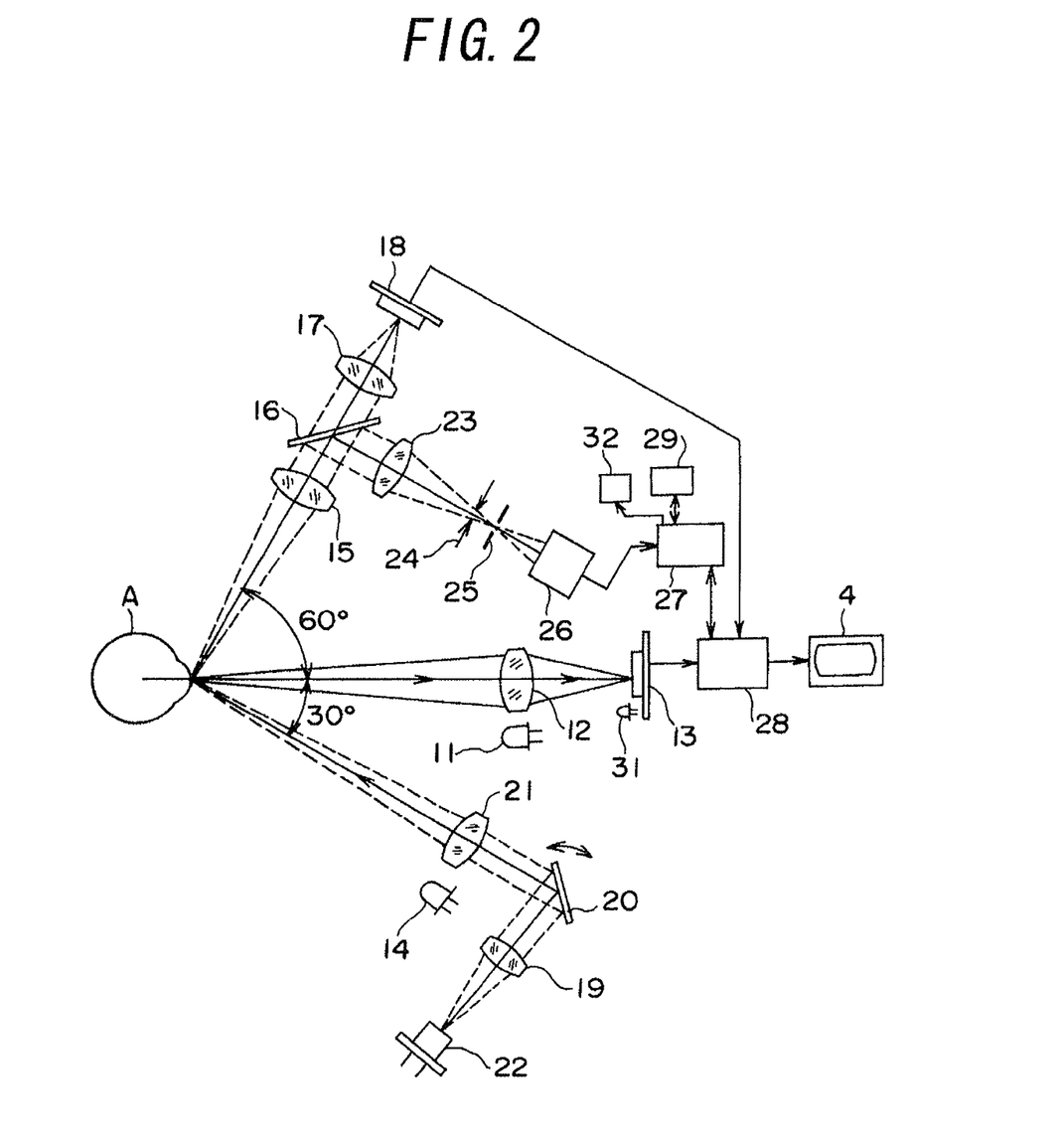
FIG. 2 illustrates a configuration of an optical system in the measurement device according to the present invention.

As illustrated in FIG. 2, the alignment and measurement optical system includes an infrared LED 11 as a reference light source irradiating an examinee's eye A with light from a front and a CCD 13 as a photographing means photographing the examinee's eye A via a camera lens 12 from the front. The optical system also includes an infrared LED 14 irradiating the examinee's eye A with light from an oblique direction (first oblique direction) at 30° to the examinee's eye A and a CCD 18 photographing the examinee's eye A via an objective lens 15, a half mirror 16, and a camera lens 17 from an oblique direction at 60° to the examinee's eye A on an opposite side to the infrared LED 14. The optical system also includes a semiconductor laser 22 as a laser light source irradiating the examinee's eye A with a laser light beam via a collimating lens 19, a turnable galvano mirror 20, and a light projecting lens 21 narrowing down the light beam toward the examinee's eye A from an oblique direction at 30° to the examinee's eye A. The optical system also includes a high-sensitivity light receiving device 26 as a light receiving unit receiving scattered light of the laser light beam from the examinee's eye A via the objective lens 15, the half mirror 16, a light receiving lens 23, a shutter 24, and a light receiving mask 25 (hereinafter, the aforementioned alignment and measurement optical system is also referred to as "an optical system of the measuring unit 3").

The half mirror 16 is a mirror that allows part of light reflected or scattered in an oblique direction at 60° to the examinee's eye A to pass therethrough and part of the light to be reflected toward the light receiving lens 23. In the present embodiment, a perforated mirror may be used instead of the half mirror 16. The light receiving lens 23 is a lens that narrows down light reflected at the half mirror 16 toward the light receiving mask 25. The high-sensitivity light receiving device 26 as a light receiving unit is a photoelectric converter transmitting an electric signal in accordance with received light.

Figure 3:
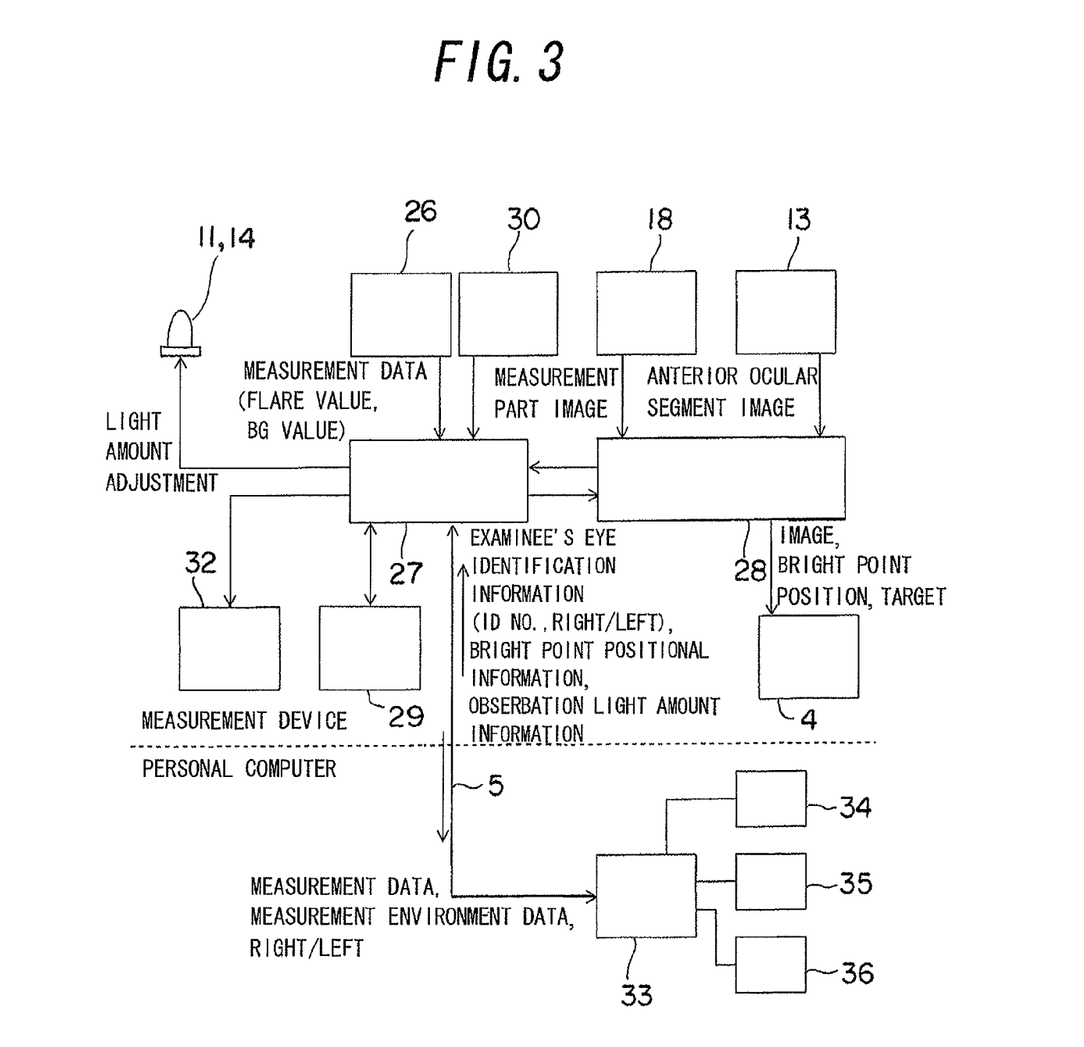
FIG. 3 illustrates a configuration of a control system in the measurement device according to the present invention.

As illustrated in FIGS. 2 and 3, the alignment and measurement control system includes a calculating unit 27 connected to the high-sensitivity light receiving device 26 and calculating optical characteristics of an anterior ocular segment from the electric signal from the high-sensitivity light receiving device 26, a switcher 28 as a switching unit connected to the CCDs 13 and 18 and the calculating unit 27 and switching image signals from the CCD 13 to the monitor 4 and those from the CCD 18 to the monitor 4, in accordance with on/off states of the infrared LEDs 11 and 14, and a main body memory 29 as a recording unit connected to the calculating unit 27. To the calculating unit 27 are respectively connected the infrared LEDs 11 and 14, a base position detector 30, and the like in addition to them. The switcher 28 is connected to the monitor 4.

Additionally, the optical system of the measuring unit 3 is provided with a fixation lamp 31 to fixate a line of sight of the examinee's eye A. The measuring unit 3 is also provided with a printer 32 to print a printed matter to be discharged from the discharging port 10.

The communication cable 5 is connected to an external personal computer 33. To the personal computer 33 are respectively connected an external printer 34, an external monitor 35, and a keyboard 36 as an inputting means.

Figure 4:
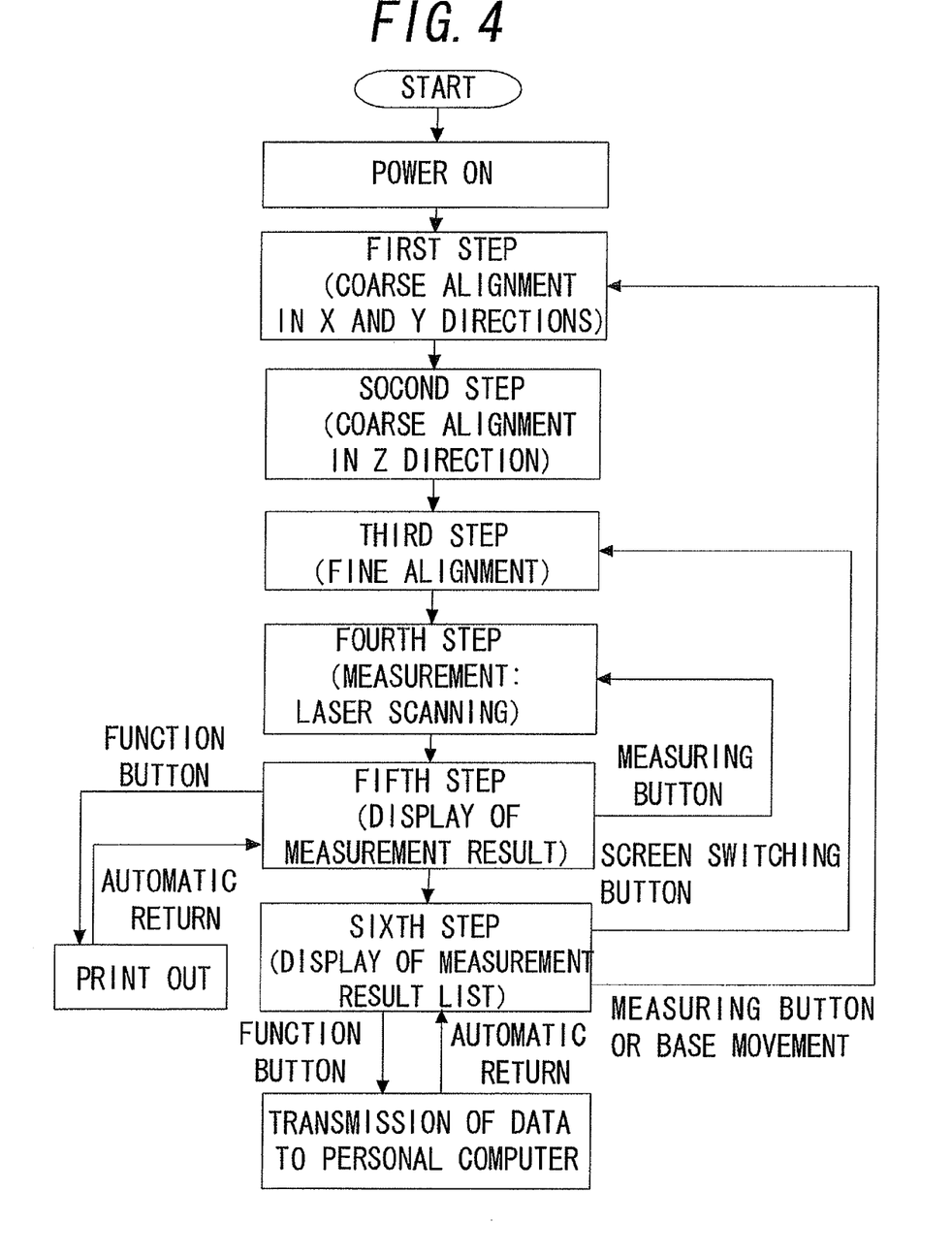
FIG. 4 illustrates an overall flow of measurement by the measurement device according to the present invention.

A method for measuring optical characteristics of the anterior ocular segment by the aforementioned ophthalmic measurement device will be described below. An overall operating flow in this method is illustrated in FIG. 4.

First, the examiner powers on the measurement device. Also, the examinee puts his/her face on the supporting base. When the base 2 moves beyond a predetermined range (e.g., the base 2 is pulled to a side of the examinee), the movement of the base 2 is detected by the base position detector 30.

[First Step (Coarse Alignment in X and Y Directions)]

At a first step, the examinee's eye A is irradiated with light from the front by the infrared LED 11 and is photographed from the front by the CCD 13 in this state, and the image is displayed on the monitor 4. In the present embodiment, a virtual image of the light emitted from the infrared LED 11 as a reference light source by a cornea of the examinee's eye A is displayed on the monitor 4 as a first bright point. Subsequently, based on a position of this first bright point, relative positions of the optical system of the measuring unit 3 and the examinee's eye A in the X and Y directions are adjusted. Specifically, the adjustment is carried out so that the position of this first bright point may approach a target displayed on the monitor 4 as a target position.

Figure 5:
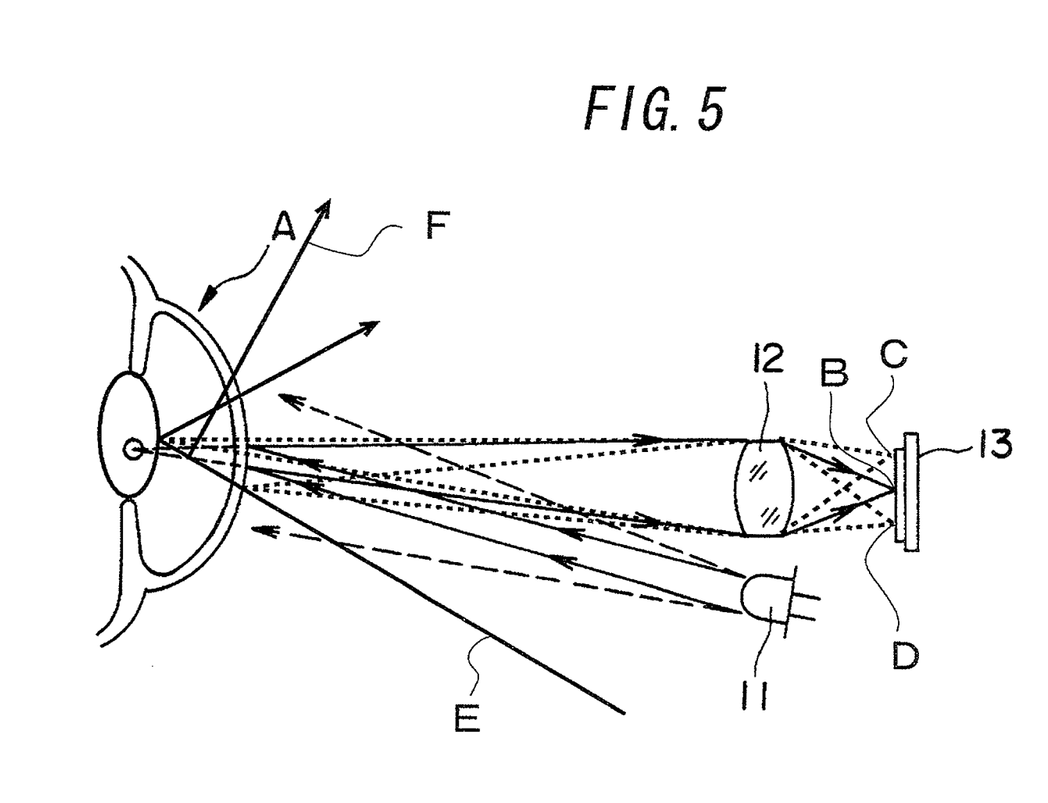
FIG. 5 illustrates an optical system to be used at first to third steps in the measurement according to the present invention.

When it is detected by the base position detector 30 that the base 2 moves beyond a predetermined range, the calculating unit 27 determines that the first step of the alignment is started and turns on the infrared LED 11 and the fixation lamp 31. By doing so, the line of sight of the examinee's eye A is fixated, and the anterior ocular segment of the examinee's eye A is irradiated with infrared light. By irradiation of this infrared light, an image photographed by the CCD 13 is displayed on the monitor 4. Also, by turning on the infrared LED 11, the virtual image of the infrared LED 11 as a light source is displayed at the anterior ocular segment of the examinee's eye A displayed on the monitor 4. An alignment optical system in the present embodiment is illustrated in FIG. 5. In FIG. 5, reflection light (first reflection light) generated by reflection of the light emitted from the infrared LED 11 at the anterior ocular segment passes through the camera lens 12, and at this time, a lens barrel of the camera lens acts as an aperture stop. Meanwhile, the infrared LED 11 is used as a light source for displaying the virtual image by the anterior ocular segment on the monitor 4 and referring to it at the time of alignment and is also an illumination for an iris.

Figure 6:
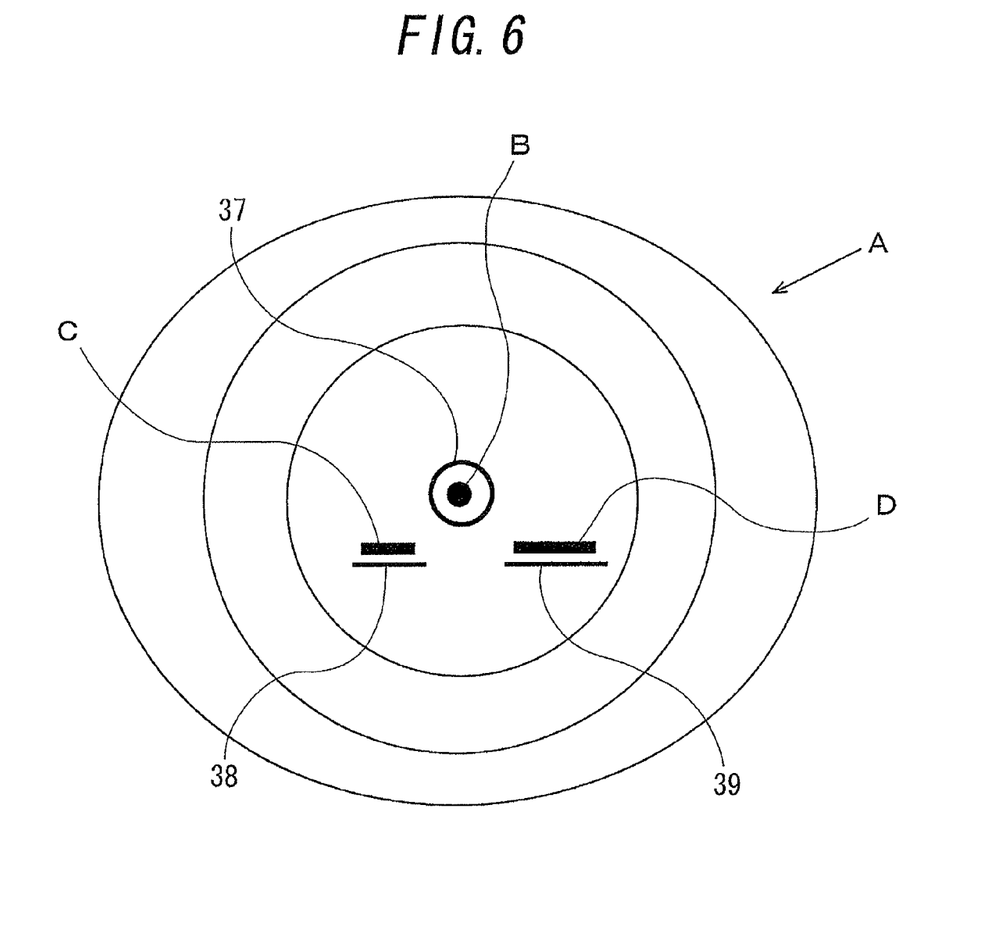
FIG. 6 illustrates an example of a screen image displayed on a monitor at the first to third steps in the measurement according to the present invention.

When the infrared LED 11 is turned on, the image of the anterior ocular segment of the examinee's eye A and the virtual image of the infrared LED 11 as the first bright point are displayed on the monitor 4, as described above. Based on the position of this first bright point, positional relationship between the examinee's eye A and the optical system of the measuring unit 3 is coarsely adjusted. This adjustment is carried out by operating the joystick 6 to cause the base 2 to be moved. Whether or not the coarse adjustment of the positional relationship between the optical system of the measuring unit 3 and the examinee's eye A is successful is determined by whether or not a position of a first bright point B is in the proximity of a target 37 provided on the monitor 4 as illustrated in FIG. 6. When the examiner determines that the positional relationship between the examinee's eye A and the optical system of the measuring unit 3 in the X and Y directions is coarsely adjusted successfully based on the first bright point, a coarse adjustment of positional relationship in the Z direction is then carried out as a second step.

[Second Step (Coarse Alignment in Z Direction)]

At a second step, relative positions of the optical system of the measuring unit 3 and the examinee's eye A in the Z direction are adjusted. In a case where it is determined at the first step that the relative positions of the examinee's eye A and the optical system of the measuring unit 3 in the X and Y directions are coarsely adjusted successfully, the examiner then operates the joystick 6 so that the first bright point may be the smallest in size while maintaining the position of the measuring unit 3 in the X and Y directions to coarsely adjust the relative positions of the optical system of the measuring unit 3 and the examinee's eye A in the Z direction. The reason for this is that, in the optical system of the measuring unit 3, positional relationship between the infrared LED 11 and the semiconductor laser 22 is set in advance so that laser light emitted from the semiconductor laser 22 may be condensed at a measuring point when the first bright point is displayed smallest.

[Third Step (Fine Alignment)]

At a third step, accurate alignment is carried out with use of laser light emitted from the semiconductor laser 22. When the examiner determines at the second step that the coarse alignment in the Z direction is completed, the examiner presses the measuring button 8. In response to it, the calculating unit 27 turns on the semiconductor laser 22 and the infrared LED 14. At this time, the semiconductor laser 22 is set to emit light with a smaller amount of light than that at the time of measurement. Also, the calculating unit 27 causes the galvano mirror 20 to be turned. This causes the laser irradiation light from the semiconductor laser 22 to scan a predetermined range of the examinee's eye A. At this stage, a background value is measured by the high-sensitivity light receiving device 26. This background value is signal intensity in a state in which laser light is emitted, but in which scanning at a measurement region has not been performed.

At this time, as illustrated in FIG. 5, reflection light (second reflection light) at the cornea of the examinee's eye A and reflection light (third reflection light) at a crystalline lens, both of which are generated by reflection of laser light E emitted from the semiconductor laser 22, respectively pass through the camera lens 12 and are formed into images on the CCD 13. These are observed as a second bright point C and a third bright point D on the monitor 4 as illustrated in FIG. 6. Meanwhile, at this time, since the laser light E is scanning by turning of the galvano mirror 20, the second bright point C and the third bright point D are displayed on the monitor 4 as linear bright points extending in the horizontal direction corresponding to the scanning direction. Subsequently, the examiner finely adjusts positional relationship between the examinee's eye A and the optical system of the measuring unit 3 with use of the joystick 6 so that the first bright point B may be located in the ring-like target 37 and so that the target 37 may be located between the second bright point C and the third bright point D in the horizontal direction (X direction).

At this time, since targets 38 and 39, which are optimal positions of the second bright point C and the third bright point D, are displayed on the monitor 4, it is preferable to finely adjust the positional relationship between the examinee's eye A and the optical system of the measuring unit 3 with use of the joystick 6 so that the second bright point C and the third bright point D may be placed on the respective targets 38 and 39. Also, at this time, in a case where measuring environment data for an identical examinee's eye of an identical examinee is stored in the past, pressing a predetermined function button 9 may cause the amounts of light of the respective light sources and the positions of the targets 37, 38, and 39 on the monitor 4 for observation to be determined based on the corresponding data.

The calculating unit 27 determines whether or not the alignment is favorable from the difference and the height level of the background value depending on the irradiation position of the laser light E, and in a case where the calculating unit 27 determines that the alignment is favorable, the blinking speeds or the display colors of the targets 37, 38, and 39 are changed, for example. This enables the examiner to confirm that the device is in a measurable state.

[Fourth Step (Measurement)]

After the fine alignment is ended, optical characteristics of the anterior ocular segment of the examinee's eye A are measured. Immediately before performing measurement actually, the calculating unit 27 stores in the main body memory 29 alignment information such as the light amounts of the infrared LED 11 and the semiconductor laser 22 and the positions of the first bright point B, the second bright point C, and the third bright point D displayed on the monitor 4 at the time of the end of the third step.

Measurement may be started automatically or manually. Meanwhile, as examples of a mode allowing measurement to be started either automatically or manually, an auto mode, a semi-auto mode, and a manual mode are raised.

In the auto mode, when the calculating unit 27 determines that the alignment is sufficiently favorable, measurement is started automatically. In this case, no manual operations such as the measuring button 8 are required. Also, in this case, the measuring button 8 will not function even if the measuring button 8 is pressed by the examiner.

In the semi-auto mode, when the calculating unit 27 determines that the alignment is sufficiently favorable, and the examiner presses the measuring button 8, measurement is started. In this case, the examiner can start measurement with reference to signals representing favorability of the alignment such as the blinking speeds or the display colors of the targets on the monitor 4.

In the manual mode, regardless of the determination at the calculating unit 27, the examiner refers to the blinking speeds or the display colors of the targets on the monitor 4 representing favorability of the alignment and presses the measuring button 8 at right timing to start measurement. A first round of measurement is performed in either mode.

Figure 7:
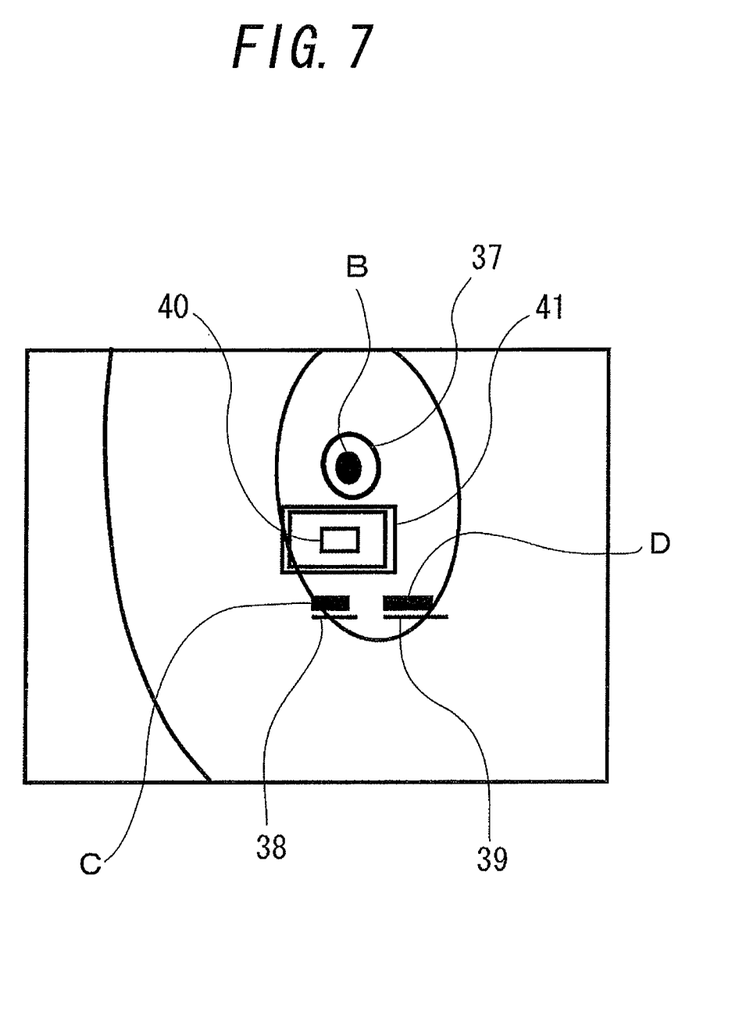
FIG. 7 illustrates an example of a screen image displayed on the monitor at a fourth step in the measurement according to the present invention.

When measurement is started, intensity of the laser light E emitted from the semiconductor laser 22 is heightened to intensity for measurement. Also, the calculating unit 27 displays a measurement window 40 illustrated in FIG. 7 on the monitor 4 via the switcher 28. The measurement window 40 represents a light receiving range of the high-sensitivity light receiving device 26 determined by an aperture width of the light receiving mask 25. By turning of the galvano mirror 20, the laser light E scans in a frame 41 in FIG. 7 containing the measurement window 40, and scattered light F by the anterior ocular segment is measured by the high-sensitivity light receiving device 26.

[Fifth Step (Display of Measurement Result)]

Figure 8:
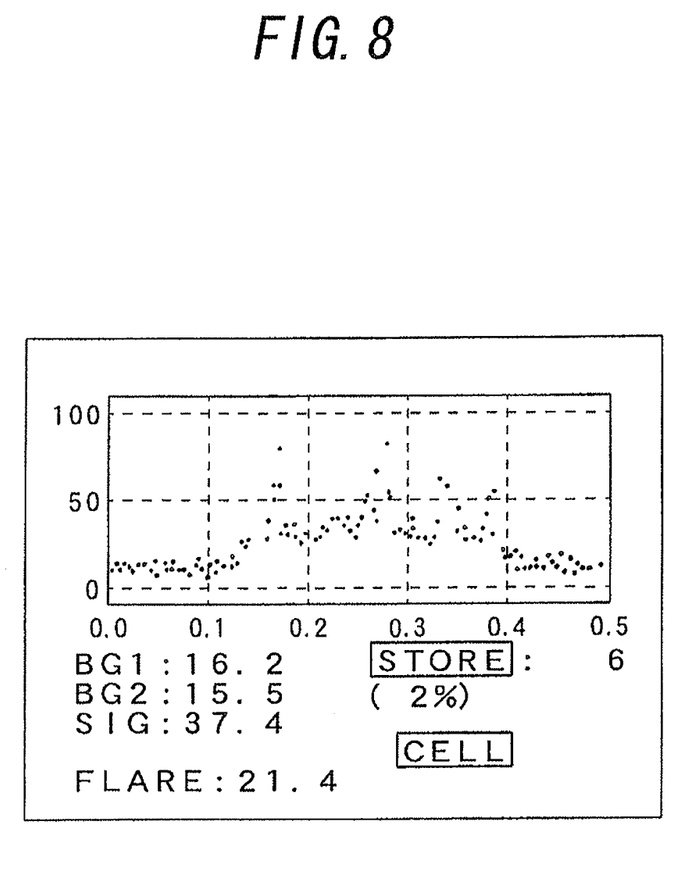
FIG. 8 illustrates an example of a measurement result displayed at a fifth step in the measurement according to the present invention.

In any of the above measurement modes, when the measurement is ended, a measurement result is recorded in the main body memory 29, and a measurement result as illustrated in FIG. 8 is displayed on the monitor 4. When a predetermined function button 9 is pressed in a state in which the measurement result is displayed on the monitor 4, the measurement result in FIG. 8 is printed by the printer 32, and a printed matter is discharged from the discharging port 10. When the measuring button 8 is pressed at this time, the procedure returns to the state of the aforementioned fourth step to enable repeated measurement. The optical characteristics of the anterior ocular segment of the examinee's eye A are measured several times as needed.

[Sixth Step (Display of Measurement Result List)]

Figure 9:
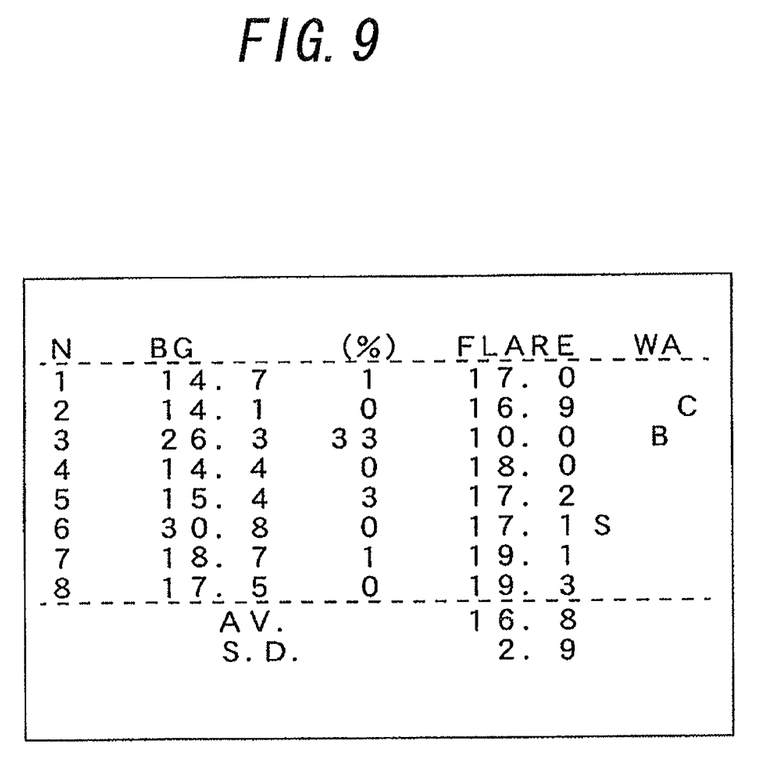
FIG. 9 illustrates an example of a list of measurement results displayed at a sixth step in the measurement according to the present invention.

When the screen switching button 7 is pressed after the measurement is performed once or several times, a table representing a list of values of measurement results as illustrated in FIG. 9 is displayed on the monitor 4. Also, the fixation lamp 31 is turned off. When a predetermined function button 9 is pressed in a state in which the measurement results are displayed on the monitor 4, the measurement results in FIG. 9 are printed by the printer 32, and a printed matter is discharged from the discharging port 10. Also, when a predetermined function button 9 is pressed in a state in which the list of the measurement results is displayed on the monitor 4, data of the measurement results is transmitted to the personal computer 33.

Subsequently, a screen confirming whether the alignment information at the aforementioned fourth step as well as the measurement result data is to be recorded is displayed on the monitor 4. Whether or not it is recorded is specified by operating a function button 9. In a case where nothing is specified, the aforementioned alignment information is not recorded, and only the measurement result data is recorded in the main body memory 29.

Figure 10:
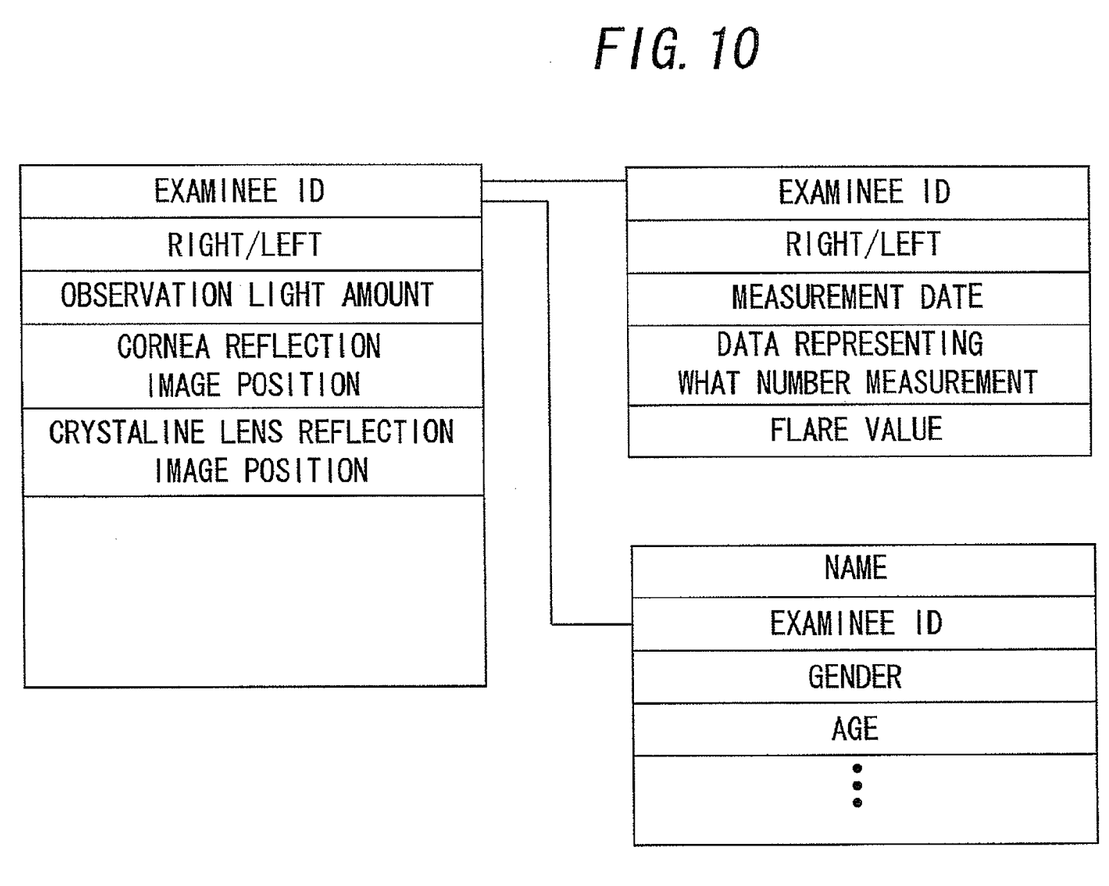
FIG. 10 illustrates an example of data relating to alignment, data relating to an examinee and an examinee's eye, and correlation of these recorded at the sixth step in the measurement according to the present invention.

When recording the alignment information as well as the measurement result data is specified, the measurement result data, data relating to the alignment, and data relating to the examinee and the examinee's eye A are correlated with one another and are recorded in the main body memory 29. The aforementioned data relating to the alignment includes light amounts of the infrared LED 11 and the infrared LED 14 recorded at the time of measurement, positions of respective images extracted and obtained by image processing of the first bright point B, the second bright point C, and the third bright point D in an image displayed on the monitor 4 and luminance of the images, and the like. Also, the aforementioned data relating to the examinee and the examinee's eye A includes an examinee's ID identifying the individual examinee, data of right or left eye, and the like (refer to FIG. 10). Data recorded in the main body memory 29 can be transmitted to the personal computer 33 by an operation of a function button 9 and can be recorded in the personal computer 33.

[Remeasurement]

Subsequently, when the base 2 is moved largely, or when the measuring button 8 is pressed, display of the monitor 4 is returned to one at the first step. At this time, the content recorded in the main body memory 29 is deleted, but a message confirming whether the deletion is allowed is displayed on the monitor 4 for the prevention of erroneous deletion. At this time, when a predetermined function button 9 is pressed, the data in the main body memory 29 is deleted. When the screen switching button 7 is pressed, display of the monitor 4 is returned to one at the third step, and measurement of the identical examinee's eye A is performed. In this case, the data in the main body memory 29 is not deleted.

The present embodiment is configured to adjust relative positions of the optical system of the measuring unit 3 and the examinee's eye A by utilizing the bright point (the first bright point B) corresponding to the virtual image by irradiation of the examinee's eye A with light from the front and the two bright points (the second bright point C and the third bright point D), which are real images by irradiation of the examinee's eye A with laser light from the oblique direction, by light generated by reflection of the light at the cornea of the examinee's eye A and light generated by reflection of the light at the crystalline lens of the examinee's eye A. Thus, positional adjustment is carried out based on the three kinds of information from the two directions, which enables more highly accurate alignment than in a conventional measurement device. Accordingly, at the time of measurement of optical characteristics of the anterior ocular segment of the examinee's eye A, highly reproducible measurement can be performed.

Also, in the present embodiment, the virtual image by irradiation with the light from the front and the real images by the light generated by reflection of the laser light E from the oblique direction at the cornea and the crystalline lens of the examinee's eye A are photographed at the CCD 13 provided at the front of the examinee's eye A and are displayed on the monitor 4. Thus, the examiner does not need to switch the display screens in the middle of alignment. Also, since the examiner can carry out the alignment with use of the display screen photographed from the front in a state of facing the examinee, the examiner is less likely to lose the sense of direction in the alignment operation. This eliminates inconvenience in the alignment operation caused by a difference between a direction in which the examiner looks and a direction in which the examiner desires to operate, which further facilitates the alignment operation.

Also, in the present embodiment, since the measurement result, the data relating to the alignment, and the data relating to the examinee's eye A and the examinee are correlated with one another and are recorded in the main body memory 29, alignment conditions and previous measurement results can be read out collectively from the examinee's state, which is further effective in understanding the course of the examinee's eye A and organizing and utilizing the data.

Also, in the present embodiment, since the ophthalmic measurement device and the personal computer 33 are connected, the measurement result, the data relating to the alignment, and the like can be taken out of the ophthalmic measurement device. Thus, the measurement result of the examinee's eye A, the alignment conditions, and the information on the course of the examinee's eye A can be shared among plural examiners. Thus, accurate measurement of optical characteristics of the anterior ocular segment can be performed by any of the examiners. Also, from the standpoint of the examinee, the examinee can undergo the aforementioned accurate measurement by the nearest ophthalmologist, which can enhance the examinee's convenience regarding measurement.

REFERENCE SIGNS LIST 1 fixed base
2 base
3 measuring unit
4 monitor
5 communication cable
6 joystick
7 screen switching button
8 measuring button
9 function button
10 discharging port
11, 14 infrared LED
12, 17 camera lens
13, 18 CCD
15 objective lens
16 half mirror
19 collimating lens
20 galvano mirror
21 light projecting lens 22 semiconductor laser
23 light receiving lens
24 shutter
25 light receiving mask
26 high-sensitivity light receiving device
27 calculating unit
28 switcher
29 main body memory
30 base position detector
31 fixation lamp
32 printer
33 personal computer
34 external printer
35 external monitor
36 keyboard
37 target representing an optimal position of a first bright point
38 target representing an optimal position of a second bright point
39 target representing an optimal position of a third bright point
40 measurement window
41 frame
A examinee's eye
B first bright point
C second bright point
D third bright point
E laser light
F measured (scattered) light

What is claimed is:

1. An ophthalmic measurement device measuring optical characteristics of an anterior ocular segment of an examinee's eye comprising:
   a laser light source irradiating the anterior ocular segment of the examinee's eye with a laser light beam from an oblique direction to the examinee's eye;
   a light receiving unit receiving scattered light of the laser light beam scattered at the anterior ocular segment and converting the scattered light into an electric signal; and
   a calculating unit calculating the optical characteristics of the anterior ocular segment from the electric signal, the ophthalmic measurement device further comprising:
   a reference light source irradiating the examinee's eye with light from a front of the examinee's eye;
   a photographing unit photographing the examinee's eye from a front;
   a positional adjusting unit adjusting relative positions of an optical system comprising the laser light source, the light receiving unit, the reference light source, and the photographing unit and the examinee's eye; and
   a displaying unit for displaying an image photographed by the photographing unit,
   wherein, the positional adjusting unit is capable of adjusting relative positions of the examinee's eye and the optical system by utilizing:
   first reflection light generated by reflection of light emitted from the reference light source at a cornea of the examinee's eye;
   second reflection light generated by reflection of laser light emitted from the laser light source at the cornea of the examinee's eye; and
   third reflection light generated by reflection of laser light emitted from the laser light source at a crystalline lens of the examinee's eye,
   wherein, the positional adjusting unit is further capable of adjusting relative positions of the examinee's eye and the optical system by:
   setting an approximate position of a first bright point corresponding to a virtual image of the reference light source based on the first reflection light generated by reflection of light emitted from the reference light source at the cornea of the examinee's eye formed by the photographing unit and displayed on the displaying unit with respect to a first target position,
   setting an approximate position of a second bright point corresponding to the second reflection light generated by reflection of laser light emitted from the laser light source at the cornea of the examinee's eye formed by the photographing unit and displayed on the displaying unit with respect to a second target position, and
   setting an approximate position of a third bright point corresponding to the third reflection light generated by reflection of laser light emitted from the laser light source at the crystalline lens of the examinee's eye formed by the photographing unit and displayed on the displaying unit with respect to a third target position.

2. The ophthalmic measurement device according to claim 1, wherein at least a target representing a target position of the first bright point is displayed on the displaying unit.

3. The ophthalmic measurement device according to claim 2, wherein light emitted from the reference light source has a wavelength in the infrared region.

4. The ophthalmic measurement device according to claim 3, wherein intensity of laser light emitted from the laser light source at the time of adjustment of the relative positions is lower than intensity of laser light emitted from the laser light source at the time of measurement of the optical characteristics of the examinee's eye.

5. The ophthalmic measurement device according to claim 2, wherein intensity of laser light emitted from the laser light source at the time of adjustment of the relative positions is lower than intensity of laser light emitted from the laser light source at the time of measurement of the optical characteristics of the examinee's eye.

6. The ophthalmic measurement device according to claim 1, wherein light emitted from the reference light source has a wavelength in the infrared region.

7. The ophthalmic measurement device according to claim 6, wherein intensity of laser light emitted from the laser light source at the time of adjustment of the relative positions is lower than intensity of laser light emitted from the laser light source at the time of measurement of the optical characteristics of the examinee's eye.

8. The ophthalmic measurement device according to claim 1, wherein intensity of laser light emitted from the laser light source at the time of adjustment of the relative positions is lower than intensity of laser light emitted from the laser light source at the time of measurement of the optical characteristics of the examinee's eye.

* * * * *